United States Patent
Barbera-Guillem et al.

(12) 
(10) Patent No.: US 6,319,607 B1
(45) Date of Patent: *Nov. 20, 2001

(54) PURIFICATION OF FUNCTIONALIZED FLUORESCENT NANOCRYSTALS

(75) Inventors: Emilio Barbera-Guillem, Powell; Stephanie L. Castro, Columbus, both of OH (US)

(73) Assignee: Bio-Pixels Ltd., Westerville, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/590,421

(22) Filed: Jun. 8, 2000

Related U.S. Application Data

(63) Continuation-in-part of application No. 09/372,729, filed on Aug. 11, 1999, now Pat. No. 6,114,038.
(60) Provisional application No. 60/107,829, filed on Nov. 10, 1998.

(51) Int. Cl.[7] ............... A61K 49/00; B05D 7/00; B32B 9/00; B32B 9/04; H01L 29/04
(52) U.S. Cl. ............ 428/402.24; 428/404; 257/65; 257/614; 257/642; 427/213.3; 427/214; 427/215; 427/220; 424/9.1; 424/9.32; 424/9.36; 424/9.42; 424/9.6

(58) Field of Search .............. 428/402.24, 404; 257/65, 614, 642; 427/213.3, 214, 215, 220; 424/9.1, 9.32, 9.36, 9.42, 9.6

(56) References Cited

U.S. PATENT DOCUMENTS

| | | |
|---|---|---|
| 5,990,479 | 11/1999 | Weiss et al. . |
| 6,114,038 | 9/2000 | Casrto et al. .................. 428/402.24 |
| 6,207,392 | 3/2001 | Weiss et al. . |

OTHER PUBLICATIONS

Bruchez Jr. et al., Semiconductor nanocrystals as fluorescent biological labels, Sep. 1998, Science, 281:2013–2015.
Chan et al., Quantam dot bioconjugates for ultrasensitive nonisotopic detection, Sep. 1998, Science, 281:2016–2018.

*Primary Examiner*—Nathan M. Nutter
(74) *Attorney, Agent, or Firm*—M. Bud Nelson

(57) ABSTRACT

Provided are methods for purifying functionalized fluorescent nanocrystals having affinity ligand operably bound thereto by using a solid support matrix in a reactor through which solutions are circulated, and by using an immobilized solid phase formed by operably binding functionalized fluorescent nanocrystals to the solid support matrix. Also provided are purified functionalized fluorescent nanocrystals having affinity ligand operably bound thereto which are purified using the methods according to the present invention to be substantially free of free affinity ligand.

34 Claims, No Drawings

PURIFICATION OF FUNCTIONALIZED FLUORESCENT NANOCRYSTALS

This is a continuation-in-part application based on U.S. Ser. No. 09/372,729 filed Aug. 11, 1999 and now U.S. Pat. No. 6,114,038 which is a nonprovisional application based on U.S. Ser. No. 60/107,829, filed Nov. 10, 1998 the disclosures of which are herein incorporated by reference.

FIELD OF THE INVENTION

This invention relates generally to fluorescent nanocrystals; and more particularly, to a novel method for purifying, or synthesizing and purifying, functionalized fluorescent nanocrystals having affinity ligand operably bound thereto using a solid support system.

BACKGROUND OF THE INVENTION

Typically, conventional fluorescent dyes (e.g., fluorescein, rhodamine, phycoerythrin, and the like) are used for labeling microspheres. These conventional fluorescent dyes typically have an excitation spectrum that may be quite narrow; hence, it is often difficult to find a wave-length spectrum of light suitable for simultaneously exciting several different fluorescent labels (e.g., differing in color of fluorescence emission). However, even when a single light source is used to provide a excitation wave-length spectrum (in view of the spectral line width), often there is insufficient spectral spacing between the emission optima of different species (e.g., differing in color) of fluorescent dyes to permit individual and quantitative detection without substantial spectral overlap. Additionally, conventional fluorescent dyes are susceptible to photobleaching which limits the time in which a fluorescent signal can be detected, and limits time-resolved fluorescence (fluorescent signal integration over time). Additional limitations of fluorescent dyes include fluorescence quenching, and shifts in fluorescence emission spectra, depending on the environment in which dyes are excited.

Fluorescent nanocrystals comprising either semiconductor nanocrystals or doped metal oxide nanocrystals have been reported to resist photobleaching, share an excitation wavelength spectrum, and are capable of emitting fluorescence of high quantum yield and with discrete peak emission spectra. However, these nanocrystals lack sufficient solubility in aqueous-based environments required in fluorescence-based biological assays; i.e., in aqueous-based environments, the nanocrystals interact together in forming aggregates, which leads to irreversible flocculation of the nanocrystals. As disclosed in detail in U.S. application Ser. Nos. 09/372,729 and 09/577,761 (the disclosures of which are herein incorporated by reference), functionalized fluorescent nanocrystals comprise fluorescent nanocrystals which have been functionalized by the addition of a plurality of molecules; and preferably, the molecules are selected from an amino acid, a carboxylic acid, and a combination thereof. A plurality of these molecules, when operably bound to a fluorescent nanocrystal, functionalizes the fluorescent nanocrystal to become water-soluble, as well as provides reactive functionalities which may be used to operably bind one or more molecules of affinity ligand. Functionalized fluorescent nanocrystals, comprising affinity ligand operably bound thereto, may be placed in contact with a sample being analyzed in a biological assay for the presence or absence of a substrate for which the affinity ligand has binding specificity. Contact, and subsequent binding, between affinity ligand of the functionalized fluorescent nanocrystals and the substrate, if present in the sample, results in a complex comprising the functionalized fluorescent nanocrystals-substrate which can emit a detectable fluorescence signal for quantitation, visualization, or other form of detection.

However, current methods of functionalizing fluorescent nanocrystals with affinity ligand suffer from a serious drawback. Even with a high efficiency of operably binding functionalized fluorescent nanocrystals with affinity ligand, the coupling reaction may result in a significant number of functionalized fluorescent nanocrystals which do not become operably bound to affinity ligand, and molecules of affinity ligand which do not become operably bound to functionalized fluorescent nanocrystals ("free affinity ligand"); a phenomenon referred to as "failed coupling". In a biological assay in which an amount of substrate is to be detected using a detection reagent which contains both functionalized fluorescent nanocrystals having affinity ligand operably bound thereto, and free affinity ligand, free affinity ligand can compete with the affinity ligand of functionalized fluorescent nanocrystals for binding the substrate. Particularly in instances when a minute amount of substrate is present, the effect of binding substrate by free affinity ligand in the detection reagent can lead to an undesirable and significant loss of sensitivity in the assay. In contrast, functionalized fluorescent nanocrystals which are not operably bound to affinity ligand will be washed away from a detection system, and hence, do not pose a significant problem if present in a detection reagent.

Thus, there remains a need for a process of purifying functionalized fluorescent nanocrystals substantially free of free affinity ligand that may be present after a step of operably binding affinity ligand to the functionalized fluorescent nanocrystals. Also needed is a purification method which is simple, uses relatively few reagents, and provides functionalized fluorescent nanocrystals having affinity ligand operably bound thereto at a high level of purity for use in fluorescence-based detection systems.

SUMMARY OF THE INVENTION

The present invention overcomes the problems outlined above by providing methods for producing functionalized fluorescent nanocrystals having affinity ligand operably bound thereto which are purified from free affinity ligand. Thus, it is a primary object of the present invention to provide a process for preparing functionalized fluorescent nanocrystals using a solid support in a reactor, such as in the form of a column, through which solutions are circulated in a continuous flow process of purification.

It is another object of the present invention to provide a system in which a solid support matrix, such as contained in a reactor, is used to operably bind and immobilize functionalized fluorescent nanocrystals in forming a solid phase, and then free affinity ligand that may be present is flowed out of the reactor in a solution. In a subsequent step, the functionalized fluorescent nanocrystals are separated from the solid phase, and then flowed out of the reactor.

It is another object of the present invention to provide a method and system for synthesizing functionalized fluorescent nanocrystals, immobilized as part of a solid phase, to be operably bound to affinity ligand; and then purifying the resultant functionalized fluorescent nanocrystals to be substantially free of free affinity ligand by flowing the free affinity ligand through the solid phase and out of the system.

It is another object of the present invention to provide a method and system for purifying functionalized fluorescent nanocrystals operably bound to affinity ligand by flowing free affinity ligand that may be present through the solid phase and out of the system so that the resultant functionalized fluorescent nanocrystals are substantially free of free affinity ligand.

The above and other objects, features, and advantages of the present invention will be apparent in the following Detailed Description of the Invention.

DETAILED DESCRIPTION OF THE INVENTION

Definitions

By the term "affinity ligand" is meant, for purposes of the specification and claims, to mean a molecule which has binding specificity and avidity for a molecular component of, or associated with, an analyte. In general, affinity ligands are known to those skilled in the art to include, but are not limited to, lectins or fragments (or derivatives) thereof which retain binding function; monoclonal antibodies ("mAb", including chimeric or genetically modified monoclonal antibodies (e.g., "humanized")); peptides; aptamers; nucleic acid molecules (including, but not limited to, single stranded RNA or single-stranded DNA, single-stranded nucleic acid hybrids, or nucleobases); avidin, or streptavidin, or avidin derivatives; and the like. The invention may be practiced using a preferred affinity ligand (e.g., a mAb) to the exclusion of affinity ligands other than the preferred affinity ligand. The term "monoclonal antibody" is also used herein, for purposes of the specification and claims, to include immunoreactive fragments or derivatives derived from a mAb molecule, which fragments or derivatives retain all or a portion of the binding function of the whole mAb molecule. Such immunoreactive fragments or derivatives are known to those skilled in the art to include F(ab')$_2$, Fab', Fab, Fv, scFV, Fd' and Fd fragments. Methods for producing the various fragments or derivatives from mAbs are well known in the art (see, e.g., Plückthum, 1992, *Immunol. Rev.* 130:152–188). For example, F(ab')$_2$ can be produced by pepsin digestion of the monoclonal antibody, and Fab' may be produced by reducing the disulfide bridges of F(ab')$_2$ fragments. Fab fragments can be produced by papain digestion of the monoclonal antibody, whereas Fv can be prepared according to methods described in U.S. Pat. No. 4,642,334. Single chain antibodies can be produced as described in U.S. Pat. No. 4,946,778. Aptamers can be made using methods described in U.S. Pat. No. 5,789,157 (herein incorporated by reference). Lectins, and fragments thereof, are commercially available.

By the term "solid phase" is meant, for purposes of the specification and claims to refer to solid support matrix operably bound to functionalized fluorescent nanocrystals.

By the terms "solid support matrix" and "matrix" are used synonymously to mean, for purposes of the specification and claims to refer to any material that is used as affinity matrices or supports for solid phase syntheses and/or solid phase purifications, as known to those skilled in the art. The matrix may be particulate or may be in the form of a continuous surface. A matrix comprising a continuous surface may include, but is not limited to, a sheet or strip of the material. When particulate, the material comprises particles of a shape that is preferably, but need not be limited to, spherical such as beads, microparticles, or agglomerated microfibers. The material may comprise a composition that includes, but is not limited to glass, silica, a glass/polymer composite (see, e.g., U.S. Pat. No. 5,507,990), controlled pore glass beads, latex, acrylic, a thermoplastic (e.g., one or more of polystyrenes, polyvinyl chloride, polyacrylate, nylon, substituted styrenes, polyamides, polycarbonate, polymethylacrylic acids, polyaldehydes, and the like), and a combination thereof. In a preferred embodiment, the matrix comprises particles, wherein a particle has an average diameter in a range of from about 0.05 micron ($\mu$m) to about 500 $\mu$m; and most preferably, in a range of from about 0.1 $\mu$m to about 100 $\mu$m. A preferred solid support matrix comprises amine-activated glass beads having an average diameter in the range of from about 1 $\mu$m to about 100 $\mu$m. As will be appreciated by those skilled in the art, the composition, shape, size, and density of the material comprising the matrix may vary depending on factors such as the reactor in which is housed the matrix, the solutions used in the process according to the present invention, and the type of functionalized fluorescent nanocrystals used in the method. Depending on the composition of the matrix, typically the matrix will comprise one or more types of reactive functionalities which react with reactive functionalities of the functionalized fluorescent nanocrystals resulting in the functionalized fluorescent nanocrystals being operably bound, in a detachable manner, to the solid support matrix. In a preferred embodiment, the one or more types of reactive functionalities present on the surface of the solid support matrix comprises a plurality of carboxyl-reactive groups, a plurality of amine-reactive groups, amine groups, or a combination thereof. A preferred solid support matrix may be used to the exclusion of a solid support matrix other than the preferred solid support matrix.

By the term "functionalized fluorescent nanocrystals" is meant, for purposes of the specification and claims to refer to nanocrystals comprising semiconductor nanocrystals or doped metal oxide nanocrystals, wherein the nanocrystals are operably bound to, and functionalized by the addition of, a plurality of molecules which provide the functionalized fluorescent nanocrystals with reactive functionalities. The reactive functionalities enable the functionalized fluorescent nanocrystals to become operably bound to one or more of: reactive functionalities of solid support matrix, and reactive functionalities of affinity ligand. In a preferred embodiment, the plurality of molecules is selected from the group consisting of carboxylic acid, diaminocarboxylic acid, a monoaminocarboxylic acid, an amino acid, and a combination thereof. A preferred type of molecule may be used to the exclusion of molecules other than the preferred type of molecule. In a preferred embodiment, the functionalized fluorescent nanocrystals are sufficiently soluble in an aqueous-based environment to permit the functionalized fluorescent nanocrystals to be operably bound in the system according to the present invention.

By the term "semiconductor nanocrystals" is meant, for purposes of the specification and claims to refer to quantum dots (crystalline semiconductors) comprised of a core comprised of at least one of a Group II-VI semiconductor material (of which ZnS, and CdSe are illustrative examples), or a Group III-V semiconductor material (of which GaAs is an illustrative example), a Group IV semiconductor material, or a combination thereof. In a preferred embodiment, the core of the quantum dots may be passivated with an semiconductor overlayering ("shell") uniformly deposited thereon. For example, a Group II-VI semiconductor core may be passivated with a Group II-VI semiconductor shell (e.g., a ZnS or CdSe core may be passivated with a shell comprised of YZ wherein Y is Cd or Zn, and Z is S, or Se). As known to those skilled in the art, the size of the semiconductor core correlates with the spectral range of emission. Table 1 is an illustrative example for CdSe.

TABLE 1

| Color | Size Range (nm) | Peak Emission Range |
|---|---|---|
| blue | 2.5 to 2.68 | 476 to 486 |
| green | 2.8 to 3.4 | 500 to 530 |
| yellow | 3.58 to 4.26 | 536 to 564 |
| orange | 4.9 to 6.1 | 590 to 620 |
| red | 8.6 to 10.2 | 644 to 654 |

In a preferred embodiment, the semiconductor nanocrystals are produced using a continuous flow process and system disclosed in copending U.S. application Ser. No. 09/468,418 (the disclosure of which is herein incorporated by reference), and have a particle size that varies by less than +/−4% in the average particle size. In a preferred embodiment, the semiconductor nanocrystals comprise a monodisperse population having an average particle size (as measure by diameter) in the range of approximately 1 nanometer (nm) to approximately 20 nm.

By the term "doped metal oxide nanocrystals" is meant, for purposes of the specification and claims to refer to nanocrystals comprised of: a metal oxide, and a dopant comprised of one or more rare earth elements. For example, suitable metal oxides include, but are not limited to, yttrium oxide ($Y_2O_3$), zirconium oxide ($ZrO_2$), zinc oxide (ZnO), copper oxide (CuO or $Cu_2O$), gadolinium oxide ($Gd_2O_3$), praseodymium oxide ($Pr_2O_3$), lanthanum oxide ($La_2O_3$), and alloys thereof. The rare earth element comprises an element selected from the Lanthanide series and includes, but is not limited to, europium (Eu), cerium (Ce), neodymium (Nd), samarium (Sm), terbium (Tb), gadolinium (Gd), holmium (Ho), thulium (Tm), an oxide thereof, and a combination thereof. As known to those skilled in the art, depending on the dopant, an energized doped metal oxide nanocrystal is capable of emitting light of a particular color. Thus, the nature of the rare earth or rare earths are selected in consequence to the color sought to be imparted (emitted) by a doped metal oxide nanocrystal used to label a microsphere according to the present invention. A given rare earth or rare earth combination has a given color, thereby permitting the provision of doped metal oxide nanocrystals, each of which may emit (with a narrow emission peak) a color over an entire range of colors by adjusting the nature of the dopant, the concentration of the dopant, or a combination thereof. For example, the emission color and brightness (e.g., intensity) of a doped metal oxide nanocrystal comprising $Y_2O_3$:Eu may depend on the concentration of Eu; e.g., emission color may shift from yellow to red with increasing Eu concentration. For purposes of illustration only, representative colors which may be provided are listed in Table 2.

TABLE 2

| Fluorescent Color | Dopant |
|---|---|
| blue | thulium |
| blue | cerium |
| yellow-green | terbium |
| green | holmium |
| green | erbium |
| red | europium |
| reddish orange | samarium |
| orange | neodymium |
| yellow | dysprosium |

TABLE 2-continued

| Fluorescent Color | Dopant |
|---|---|
| white | praseodymium |
| orange-yellow | europium + terbium |
| orange-red | europium + samarium |

Methods for making doped metal oxide nanocrystals are known to include, but are not limited to, a sol-gel process (see, e.g., U.S. Pat. No. 5,637,258), and an organometallic reaction. As will be apparent to one skilled in the art, the dopant (e.g., one or more rare earth elements) is incorporated into the doped metal oxide nanocrystal in a sufficient amount to permit the doped metal oxide nanocrystal to be put to practical use in fluorescence detection as described herein in more detail. An insufficient amount comprises either too little dopant which would fail to emit sufficient detectable fluorescence, or too much dopant which would cause reduced fluorescence due to concentration quenching. In a preferred embodiment, the amount of dopant in a doped metal oxide nanocrystal is a molar amount in the doped metal oxide nanocrystal selected in the range of from about 0.1% to about 25%. Doped metal oxide nanocrystals may can be excited with a single excitation light source resulting in a detectable fluorescence emission of high quantum yield (e.g., a single quantum dot having at a fluorescence intensity that may be a log or more greater than that a molecule of a conventional fluorescent dye) and with a discrete fluorescence peak. Typically, they have a substantially uniform size of less than 200 Angstroms, and preferably have a substantially uniform size in the range of sizes of from about 1 nm to about 5 nm, or less than 1 nm. In a preferred embodiment, the doped metal oxide nanocrystals are comprised of metal oxides doped with one or more rare earth elements, wherein the dopant comprising the rare earth element is capable of being excited (e.g., with ultra-violet light) to produce a narrow spectrum of fluorescence emission. In another preferred embodiment, the doped metal oxide has both fluorescent properties (when excited with an excitation light source) and magnetic properties; thus, a polymeric microsphere (which is substantially nonmagnetic) operably bound to a plurality of fluorescent nanocrystals (comprising doped metal oxide nanocrystals which are magnetic material) may form fluorescent microspheres according to the present invention which are magnetic.

By the term "operably bound" is meant, for purposes of the specification and claims, to refer to fusion or bond or an association of sufficient stability to withstand conditions encountered in the method according to the present invention for the purposes of the method, between a combination of different molecules such as, but not limited to, between a functionalized fluorescent nanocrystal and the solid support matrix, between a fluorescent nanocrystal and the molecules by which they are functionalized (e.g., carboxylic acid, diaminocarboxylic acid, or a monoaminocarboxylic acid), between a functionalized fluorescent nanocrystal and affinity ligand, and a combination thereof. As known to those skilled in the art, the bond may comprise one or more of covalent, ionic, hydrogen, van der Waals, electrostatic, and the like. As known to those skilled in the art, and as will be more apparent by the following embodiments, there are several methods and compositions in which two or more molecules may be operably bound utilizing reactive functionalities. Reactive functionalities include, but are not limited to, free chemical groups (e.g., thiol, or carboxyl, hydroxyl, amine, sulfo, etc.), and reactive chemical groups (reactive with free chemical groups).

The term "suitable conditions" is used herein, for purposes of the specification and claims, and with reference to a process of reacting two components (e.g., solid support matrix and functionalized fluorescent nanocrystals; functionalized fluorescent nanocrystals and affinity ligand), to mean those conditions under which the components may become operably bound to each other. As known to those skilled in the art, such conditions may include one or more of: a pH range of from about 3 to about 9, ionic strengths such as that ranging from distilled water to about 1 molar sodium chloride, and a temperature in the range of from about 4° C. to about 45° C.; and may further include a time sufficient for binding to occur (e.g., in a range of from about 10 minutes to about 2 hours).

By the term "diaminocarboxylic acid" is meant, for purposes of the specification and claims to refer to an amino acid that has two free amine groups. The amino acid may be a naturally occurring amino acid, a synthetic amino acid, a modified amino acid, an amino acid derivative, and an amino acid precursor (e.g., citrulline and ornithine are intermediates in the synthesis of arginine). In a preferred embodiment, the diaminocarboxylic acid contains neutral (uncharged) polar functional groups which can hydrogen bond with water, thereby making the diaminocarboxylic acid (and the quantum dot to which it is made a part of) relatively more soluble in aqueous solutions containing water than those with nonpolar functional groups. Exemplary diaminocarboxylic acids include, but are not limited to, lysine, asparagine, glutamine, arginine, citrulline, ornithine, 5-hydroxylysine, djenkolic acid, β-cyanoalanine, and synthetic diaminocarboxylic acids such as 3,4-diaminobenzoic acid, 2,3-diaminopropionic acid, 2,4-diaminobutyric acid, 2,5-diaminopentanoic acid, and 2,6-diaminopimelic acid.

By the term "amino acid" is meant, for purposes of the specification and claims to refer to a molecule that has at least one free amine group and at least one free carboxyl group. The amino acid may have more than one free amine group, or more than one free carboxyl group, or may further comprise one or more free chemical reactive groups other than an amine or a carboxyl group (e.g., a hydroxyl, a sulfhydryl, etc.). The amino acid may be a naturally occurring amino acid, a synthetic amino acid, a modified amino acid, an amino acid derivative, and an amino acid precursor. The amino acid may further be selected from the group consisting of a monoaminocarboxylic acid, and a diaminocarboxylic acid. In a preferred embodiment, the monoaminocarboxylic acid contains one or more neutral (uncharged) polar functional groups which can hydrogen bond with water, thereby making the monoaminocarboxylic acid (and the quantum dot to which it is made a part of) relatively more soluble in aqueous solutions containing water than those with non-polar functional groups. Exemplary monoaminocarboxylic acids include, but are not limited to, glycine, serine, threonine, cysteine, β-alanine, homoserine, γ-aminobutyric acid, and homocysteine.

By the term "carboxylic acid" is meant, for purposes of the specification and claims to refer to a compound having the formula $HS(CH_2)_nX$, wherein X is a carboxylate (carboxylic moiety). "n" is a number in the range of from 1 to about 20, and preferably greater than 4. In a preferred embodiment, the thiol group of the carboxylic acid can be used as a reactive functionality for the carboxylic acid to become operably bound to the nanocrystal, depending on the composition of the nanocrystal (e.g., to Cd, Zn and the like). Additionally, the carboxylic moiety of the carboxylic acid imparts water solubility to the nanocrystals. Exemplary carboxylic acids may include, but are not limited to, mercaptocarboxylic acid, or mercaptofunctionalized amines (e.g., aminoethanethiol-HCl, or 1-amino-2-methyl-2-propanethiol-HCl).

The subject of the present invention is a process for purifying functionalized fluorescent nanocrystals by using a solid support matrix in a reactor through which solutions are circulated. Preferably, the solid support matrix is immobilized in the reactor, and the solutions are flowed through an immobilized solid phase comprising functionalized fluorescent nanocrystals operably bound to the solid support matrix. Alternately, the solid phase may be formed first (e.g., outside the reactor), and the solid phase is then immobilized in the reactor. Various solutions may be flowed through the reactor, which circulate through the solid phase, in a stepwise fashion during the steps of the process so that successive solutions need not mix (e.g., such as in a continuous flow process). In a preferred embodiment, the reactor is in the form of a column which contains the solid support matrix in particulate form. In a more preferred embodiment, the solid support matrix comprises beads which are immobilized in the column by sufficiently packing the beads in the column such that they can no longer move (e.g., are restricted from moving to positions elsewhere in the column) as a solution is flowed through the column. Preferably, the column will have a cylindrical shape, wherein the size will vary depending on the scale of purification to be performed according to the method of the present invention. Likewise, as apparent to those skilled in the art, the flow rate of the solutions will vary depending on the size of the reactor and the size of the solid support matrix. Thus, a system which may be used in the method according to the present invention comprises: a solid support matrix, a reactor, and functionalized fluorescent nanocrystals having affinity ligand operably bound thereto to be purified by the method according to the present invention. The system may further comprise one or more solutions useful in the method according to the present invention. Also, the system may further comprise a solid phase formed by operably binding to the solid support matrix the functionalized fluorescent nanocrystals having affinity ligand operably bound thereto.

In one preferred embodiment, the functionalized fluorescent nanocrystals are, in a separate reaction, operably bound to affinity ligand. The reaction product, a mixture comprising functionalized fluorescent nanocrystals having affinity ligand operably bound thereto and free affinity ligand, is then subjected to purification in the method according to the present invention which purifies functionalized fluorescent nanocrystals having affinity ligand operably bound thereto apart from free affinity ligand. The general scheme for purifying functionalized fluorescent nanocrystals by this method comprises the following sequential steps:

(1) contacting a mixture comprising functionalized fluorescent nanocrystals having affinity ligand operably bound thereto, and free affinity ligand, with solid support matrix under suitable conditions for the functionalized fluorescent nanocrystals to become operably bound to solid support matrix in forming an immobilized solid phase;

(2) flowing a solution through the immobilized solid phase in removing free affinity ligand from the solid phase (e.g., flowing a solution through the solid phase, wherein free affinity ligand that may be present in the solid phase is soluble in the solution, and thus is carried out of the solid phase as the solution carrying the free affinity ligand is flowed out of the solid phase);

(3) detaching the functionalized fluorescent nanocrystals, comprising functionalized fluorescent nanocrystals having affinity ligand operably bound thereto, from the solid support matrix; and (4) flowing a solution through the solid support matrix to remove from the solid support matrix the detached functionalized fluorescent nanocrystals having affinity ligand operably bound thereto in yielding purified functionalized fluorescent nanocrystals having affinity ligand operably bound thereto (i.e., flowing a solution through the solid support matrix wherein the functionalized fluorescent nanocrystals are soluble in the solution, and thus are carried out of the solid support matrix as the solution carrying the functionalized fluorescent nanocrystals is flowed out of a reactor which contains the solid support matrix). It will be appreciated by those skilled in the art that step of detaching of the functionalized fluorescent nanocrystals, and the step of flowing of a solution through the solid support matrix to yield purified functionalized fluorescent nanocrystals having affinity ligand operably bound thereto, may comprise a single step in which a solution inducing detachment is also the solution which may be used to flow functionalized fluorescent nanocrystals having affinity ligand operably bound thereto out of the reactor containing the solid support matrix. Alternatively, the steps may comprise two independent steps, wherein a solution is flowed through the solid phase and induces the detachment; and a subsequent solution is flowed through the reactor to remove the detached functionalized fluorescent nanocrystals having affinity ligand operably bound thereto from the solid support matrix and out of the reactor. As apparent to one skilled in the art, whether it is one step or two steps depends on factors including, but not limited to, the means by which the functionalized fluorescent nanocrystals are operably bound to the solid support matrix, the means by which the functionalized fluorescent nanocrystals are detached from the solid phase, and the size of the solid phase/reactor.

In another preferred embodiment, functionalized fluorescent nanocrystals are further functionalized in the solid phase by the addition of affinity ligand thereto, and the resultant product of the reaction is then purified from free affinity ligand that may be present in the solid phase after the reaction. For example, functionalized fluorescent nanocrystals are operably bound to solid support matrix in forming a solid phase. A solution comprising affinity ligand is contacted with the solid phase so that affinity ligand becomes operably bound to functionalized fluorescent nanocrystals. The solid phase, comprising solid support matrix operably bound to functionalized fluorescent nanocrystals having affinity ligand operably bound thereto, and free affinity ligand that may be present, is then subjected to purification in the method according to the present invention. The general scheme for purifying functionalized fluorescent nanocrystals having affinity ligand operably bound thereto by this method comprises the following sequential steps:

(1) contacting functionalized fluorescent nanocrystals with solid support matrix under suitable conditions for the functionalized fluorescent nanocrystals to become operably bound to solid support matrix in forming an immobilized solid phase;

(2) contacting the solid phase with a solution comprising affinity ligand under suitable conditions for affinity ligand to become operably bound to functionalized fluorescent nanocrystals of the solid phase;

(3) flowing a solution through the solid phase in removing free affinity ligand from the solid phase;

(4) detaching the functionalized fluorescent nanocrystals, comprising functionalized fluorescent nanocrystals having affinity ligand operably bound thereto, from the solid support matrix; and (5) flowing a solution through the solid support matrix to remove from the solid support matrix the detached functionalized fluorescent nanocrystals having affinity ligand operably bound thereto in yielding purified functionalized fluorescent nanocrystals having affinity ligand operably bound thereto. Similar to the previously described embodiment, whether the detachment and subsequent removal of the detached functionalized fluorescent nanocrystals having affinity ligand operably bound thereto from the solid support matrix comprises one step or two sequential steps may depend on factors including, but not limited to, the means by which the functionalized fluorescent nanocrystals are operably bound to the solid support matrix, the means by which the functionalized fluorescent nanocrystals are detached from the solid phase, and the size of the solid phase/reactor.

In either of these embodiments, the solutions used to purify the functionalized fluorescent nanocrystals in the steps of the method preferably comprise one or more aqueous-based solutions used for solid phase syntheses and/or solid phase purifications, as known to those skilled in the art. Such solutions may include but are not limited to, water, a buffer, a salt-base solution, reagents, and the like. By either of these embodiments, the resultant purified functionalized fluorescent nanocrystals having affinity ligand operably bound thereto are substantially free of free affinity ligand (e.g., the preparation comprises less than 0.1% free affinity ligand; or free affinity ligand is not detectable by spectrophometric determination (e.g., zero value at 280 nm for protein, or at 260 nm for DNA)) as compared to functionalized fluorescent nanocrystals not purified by a method according to the present invention (e.g., 10% or greater, and often times as much as 50%, of affinity ligand present comprises free affinity ligand). In either of these embodiments, there are preferred means for operably binding functionalized fluorescent nanocrystals to solid support matrix in forming the solid phase, which means also facilitates subsequent detaching of the functionalized fluorescent nanocrystals from the solid support matrix. For example, in one preferred embodiment a cleavable linker is used to operably bind the functionalized fluorescent nanocrystals to the solid support matrix. The cleavable linker comprises two reactive functionalities, wherein one reactive functionality can be operably bound to a reactive functionality of the solid support matrix, and a second reactive functionality that can operably bind to a reactive functionality of a functionalized fluorescent nanocrystal. For example, the solid support matrix may be contacted with cleavable linker under suitable conditions for the cleavable linker to become operably bound to the solid support matrix via one of the reactive functionalities of the cleavable linker. Optionally, free (unbound) cleavable linker may be removed from the solid support matrix by washing the support matrix with a solution (i.e., flowing a solution through the solid support matrix wherein the cleavable linker is soluble in the solution, and thus is carried out of the solid matrix as the solution is flowed out of a reactor which contains the solid support matrix). The solid support matrix is then contacted with the functionalized fluorescent nanocrystals under suitable conditions for the unbound reactive functionality of a cleavable linker (the linkers being bound to the solid support matrix) to become operably bound to a reactive functionality of a functionalized fluorescent nanocrystals in a process of operably binding the functionalized fluorescent nanocrystals to the solid support matrix. A solution may then be introduced into and flowed through the solid phase in removing free affinity ligand from the solid phase. In the step in the process in which functionalized fluorescent nanocrystals are to be detached from the solid support matrix, a cleaving agent for cleaving the cleavable linker is contacted with the solid phase under conditions suitable for cleavage of the cleavable linker. As apparent to those skilled in the art, the nature and amount of cleavage agent will depend on factors such as the nature and amount of cleavable linker, and the size of the solid phase. In one preferred embodiment, a solution containing the cleaving agent may be flowed through the solid phase in contacting cleaving agent with cleavable linker, and in cleaving the cleavable linker. As the front of the solution comprising the cleaving agent moves through the solid phase, another solution may introduced into, and subsequently flowed through, the solid phase in removing the cleaved functionalized fluorescent nanocrystals from the solid support matrix.

As apparent to one skilled in the art, the cleavable linker may be selected from the group consisting of a heterobifunctional linker, and a homobifunctional linker. Generally speaking, typical cleavable linkers have a cleavable bond which is spacially located on the linker molecule between the two reactive functionalities of the cleavable linker. Exemplary commercially available cleavable linkers which may be used in the method of the present invention may include, but are not limited to, the cleavable linkers listed in Table 3. Also listed in Table 3 are the reactive functionalities (chemical groups "reactive towards") which the cleavable linker can bind, as well as an appropriate cleaving agent.

TABLE 3

| Linker | chemical name | reactive towards | cleavable by |
|---|---|---|---|
| SFAD | Sulfosuccinimidyl-[perfluoroazidobenzamido]-ethyl-1,3'-dithiopropionate | NH2, —CH bonds | thiols |
| BASED | Bis-[β-(4-azidosalicyl-amido)ethyl]disulfide | NH2, NH2 | thiols |
| BSOCOES | Bis[2(succinimidyloxycar-bonyloxy)-ethyl]sulfone | NH2, NH2 | base |
| DSP | Dithiobis[succinimidyl propionate] | NH2, NH2 | thiols |
| DST | Disuccinimidyl tartrate | NH2, NH2 | periodate |
| DTBP | Dimethyl 3,3'-dithiobispro-pionimidate hydrochloride | NH2, NH2 | thiols |
| DTSSP | 3,3'-Dithiobis [sulfosucci-nimidyl propionate] | NH2, NH2 | thiols |
| EGS | Ethylene glycol bis [succinimidylsuccinate] | NH2, NH2 | hydroxyl-amine |
| SADP | N-succinimidyl [4-azido-phenyl]-1,3'-dithiopropi-onate | NH2, NH2 | thiols |
| SAED | Sulfosuccinimidyl 2-[7-azido-4-methyl-coumarin-3-acetamido]ethyl-1,3'-dithiopropionate | NH2, NH2 | thiols |
| SAND | Sulfosuccinimidyl 2-[m-azido-o-nitro-benzamido]ethyl-1,3'-dithiopropionate | NH2, NH2 | thiols |
| SASD | Sulfosuccinimidyl-2-[p-azido-salicylamido]ethyl-1,3'-dithiopropionate | NH2, NH2 | thiols |
| PDPH | 3-[2-pyridyldithio] propionyl hydrazide | SH, carbo-hydrate | thiols |
| APDP | N-[4-(p-Azidosalicylamido) butyl]-3'(2'-pyridyldithio) propionamide | SH, NH2 | thiols |

TABLE 3-continued

| Linker | chemical name | reactive towards | cleavable by |
|---|---|---|---|
| LC-SPDP | Succinimidyl 6-[3-(2-pyri-dyldithio)-propionamido] hexanoate | SH, NH2 | thiols |
| SMPT | 4-Succinimidyloxycarbonyl-methyl-α[2-pyridyldithio] toluene | SH, NH2 | thiols |
| SPDP | N-Succinimidyl 3-[2-pyridyldithio]propionate | SH, NH2 | thiols |
| BMDB | 1,4-Bis-Maleimidyl-2,3-dihydroxybutane | SH, SH | periodate |
| DPDPB | 1,4-Di-[3'-(2'-pyridyldi-thio)propionamido]butane | SH, SH | thiols |
| DTME | Dithio-bis-maleimidoethane | SH, SH | thiols |

In another preferred embodiment, an ion-pairing comprises the reactive functionalities operably binding functionalized fluorescent nanocrystals to solid support matrix in forming the solid phase. The ion pairing also facilitates the subsequent detaching of the functionalized fluorescent nanocrystals from the solid support matrix. For example, the solid support matrix having amines as the reactive functionalities may be contacted with a mixture comprising functionalized fluorescent nanocrystals having amine-reactive groups as reactive functionalities under suitable conditions for the functionalized fluorescent nanocrystals to become operably bound to the solid support matrix. Desirably, the amine group comprises a proton which binds to an amine-reactive group, but which is induced to deprotonate by a high pH. A solution may then be introduced into and flowed through the solid phase in removing free affinity ligand from the solid phase. In the step in the process in which functionalized fluorescent nanocrystals are to be detached from the solid support matrix, a solution having a high pH is contacted with the solid phase under conditions suitable for disrupting the ionic bonding necessary for the functionalized fluorescent nanocrystals to remain operably bound to the solid support matrix. As apparent to those skilled in the art, the pH necessary to induce the ion-pairing to deprotonate will depend on factors such as the chemical nature of the ion-pairing. In one preferred embodiment, the high pH comprises a pH above about 9, and in a more preferred embodiment, the high pH comprises a pH of about 12 or greater. As the front of the solution comprising the high pH moves through the solid phase, another solution may introduced into, and subsequently flowed through, the solid phase in removing the detached functionalized fluorescent nanocrystals from the solid support matrix. In these embodiments, the operably binding between the functionalized fluorescent nanocrystals and affinity ligand remains stable when exposed to the high pH during the step in which the functionalized fluorescent nanocrystals having affinity ligand operably bound thereto are detached from the solid support matrix.

The following examples are illustrative of the methods and system of the present invention.

EXAMPLE 1

This example illustrates various functionalized fluorescent nanocrystals according to the present invention. As disclosed in detail in U.S. application Ser. No. 09/372,729 (the disclosure of which is herein incorporated by reference), fluorescent nanocrystals comprise nanocrystals which have been functionalized by the addition of a plurality of molecules; and preferably, the molecules are selected from an amino acid, a carboxylic acid, and a combination thereof. For example, the nanocrystals may comprise semiconductor nanocrystals that have a core selected from the group consisting of CdSe, CdS, and CdTe (collectively referred to as "CdX"), and may further comprise a passivating shell comprised of YZ wherein Y is Cd or Zn, and Z is S, or Se. Typically, CdX core/YZ shell quantum dots are overcoated with trialkylphosphine oxide, with the alkyl groups most commonly used being butyl and octyl. In one preferred embodiment, the CdX core/YZ shell quantum dots are treated with a large excess of mercaptocarboxylic acid in exchanging the trialkylphosphine oxide coat with a coat comprising a plurality of carboxylic acid molecules. For example, (CdSe)ZnS nanocrystals were prepared in a pyridine solution. The pyridine overcoating of the (CdX) core/YZ shell nanocrystals were exchanged with a carboxylic acid comprising mercaptocarboxylic acid. Exchange of the coating group is accomplished by treating the water-insoluble, pyridine-capped quantum dots with a large excess of neat mercaptocarboxylic acid. To accomplish this, the pyridine-capped (CdSe)ZnS quantum dots were precipitated with hexanes, and then isolated by centrifugation. The residue was dissolved in neat mercaptoacetic acid, with a few drops of pyridine added, if necessary, to form a transparent solution. Chloroform was added to precipitate the nanocrystals and wash away excess thiol. The nanocrystals were isolated by centrifugation, washed once more with chloroform, and then washed with hexanes. The residue was briefly dried with a stream of argon. The resultant nanocrystals, coated with molecules of carboxylic acid, were then soluble in water or other aqueous solutions. The nanocrystals, in an aqueous solution, were centrifuged once more, filtered through a 0.2 $\mu$m filter, degassed with argon, and stored in an amber vial. The nanocrystals may then be further functionalized by an amino acid comprising a diaminocarboxylic acid. The diaminocarboxylic acid molecules were operably bound to the carboxylic acid molecules of the nanocrystals by using commercially available crosslinking agents and methods known to those skilled in the art. For example, the carboxylic acid-coated nanocrystals were dissolved in an aqueous buffer system (pH of about 7). To the nanocrystals was added EDC (1-ethyl-3-[3-dimethylaminopropyl]carbodiimide) and sulfoNHS (sulfo-N-hydroxysuccinimide) in 500–1000 times excess. The resulting solution was stirred at room temperature for 30 minutes. Mercaptoethanol was added to neutralize unreacted EDC at 20 mM concentration and stirred for 15 minutes. The entire solution was then added dropwise, with stirring, to a solution of a diaminocarboxylic acid comprising lysine (large excess) in the same buffer; and the mixture was stirred for 2 hours at room temperature. Ethanolamine (30 mM) was added to quench the reaction; and the mixture was stirred for 30 minutes at room temperature or left overnight at 4° C. The solution was centrifuged to remove any precipitated solids, and then ultrafiltered through a 30 kD MW centrifugal filter. The resultant concentrated, fluorescent nanocrystals can be solubilized in an aqueous solution of choice. Once solubilized, the resulting solution can be stored in an amber vial under an inert gas to prevent flocculation. The fluorescent nanocrystals may be operably bound to a successive layer of amino acid molecules by, for example, repeating the procedure and reaction using EDC and sulfoNHS with the amino acid molecules comprising the successive layer.

Similarly, a nanocrystal comprising a doped metal oxide nanocrystal may be operably bound to a plurality of molecules (e.g., a carboxylic acid, and amino acid, or a combination thereof) using methods known in the art. For example, the plurality of molecules having reactive functionalities comprising free carboxyl groups can be chemisorbed, adsorbed or otherwise permanently added to the metal oxide portion of the nanocrystal. For example, the metal oxide nanocrystals are suspended in an aqueous solution of an amino acid comprising homocysteine having a pH of about 3.5 for about an hour. The reaction is then stopped by adjusting the pH to neutral, and dialyzing out the aqueous solution.

As an alternative, fluorescent nanocrystals functionalized with a plurality of homocysteine molecules were prepared as follows. Nanocrystals (e.g., (CdSe)ZnS) coated with an organic layer (e.g., mercaptoacetic acid) were treated with a molar excess of homocysteine in replacing the organic layer with a coating comprising a plurality of homocysteine molecules. The approximate number of surface Zn sites on the specific size of nanocrystals utilized was calculated. At least a 5 times molar excess of homocysteine (as compared to the number of surface Zn sites) was added to the nanocrystals, as per the following formula. Grams homocysteine=5(number of Zn surface sites) (volume of solution containing the nanocrystals) (concentration of nanocrystals in solution) (135.2). The mixture was stirred to dissolve the homocysteine, and then stored at 4° C. for 24 hours. The resultant solution was then centrifuged to remove any precipitate, and the supernatant was transferred to a centrifugal filter for the appropriate volume of supernatant (preferably, with a molecular weight cutoff of about 10 kD or below to retain the fluorescent nanocrystals coated with homocysteine). After centrifugation, and when the desired minimum volume is reached, the fluorescent nanocrystals were then rediluted in the appropriate aqueous solution (e.g., HEPES buffer) to a volume in which the original mass of homocysteine had been dissolved. The steps of filtering and redilution of the fluorescent nanocrystals in solution may be repeated to improve purity. The resultant fluorescent nanocrystals comprising homocysteine-coated nanocrystals may then be degassed by bubbling with an inert gas, and then stored at 4° C. in an amber bottle.

EXAMPLE 2

This example illustrates various embodiments of further functionalizing functionalized fluorescent nanocrystals with affinity ligand. As previously described herein, in one preferred embodiment, affinity ligand may be operably bound to functionalized fluorescent nanocrystals prior to the purification process according to the present invention. Alternatively, in another preferred embodiment, affinity ligand may be operably bound to functionalized fluorescent nanocrystals as a synthesis step in the solid phase, and then functionalized fluorescent nanocrystals having affinity ligand operably bound thereto are purified by the purification process according to the present invention. The present inventors have described in detail the operably binding of various affinity ligands to functionalized fluorescent nanocrystals in copending applications. The following are exemplary embodiments of operably binding affinity ligands to functionalized fluorescent nanocrystals.

For example, an affinity ligand selected from the group consisting of avidin, a monoclonal antibody, or a lectin (e.g., wheat germ agglutinin) have been operably linked using EDC and sulfo-NHS. More particularly, EDC functions to activate at least one reactive functionality (e.g., a carboxylate of the functionalized fluorescent nanocrystal) to catalyze its reaction with another reactive functionality such as the amine group of the affinity ligand. The functionalized fluorescent nanocrystals (1 ml, $8.1 \times 10^{-9}$ mol) were esterified by treatment with EDC ($8.1 \times 10^{-6}$ mol), followed by treatment with sulfo-NHS ($8.9 \times 10^{-6}$ mol) at ambient temperature in buffered aqueous solution (at about pH 6.9) for 10 minutes. 2-mercaptoethanol was added to the solution at a concentration of 20 mM, and the mixture was stirred for 5 minutes to quench any unreacted EDC. The functionalized fluorescent nanocrystals were then contacted with affinity ligand ($8.1 \times 10^{-9}$ mol in HEPES buffer, 1 mg/ml) with vigorous stirring, and the reaction mixture was stirred for 2 hours (e.g., conditions sufficient to form an amide bond between the EDC-activated carboxylates of the diaminocarboxylate layer of the functionalized fluorescent nanocrystals and the amine groups on the affinity ligand in forming functionalized fluorescent nanocrystals having affinity ligand operably bound thereto). Ethanolamine was added at a concentration of 30 mM to quench the coupling reaction, and the reaction mixture was stirred for 30 minutes. The resulting solution was then filtered through a 30 kD molecular weight cutoff centrifugal filter to remove excess reagents. The concentrated material was then diluted to 1 ml in buffer (e.g., HEPES) or other suitable aqueous solution.

In another illustrative embodiment, the diaminocarboxylic acid of a functionalized nanocrystal may be operably bound to a nucleobase (a single nucleobase, or to a nucleobase which is part of a nucleic acid molecule). There are nucleobases known to those skilled in the art to have a free carboxyl-reactive group (e.g., amine group such as 3' (2')-amino-modified nucleosides, 3' (2')-amino-modified nucleotides) which can be operably bound to a free carboxyl group of the functionalized fluorescent nanocrystals using methods known in the art (e.g., treatment with EDC, followed by treatment with sulfo-NHS, as previously described herein).

EXAMPLE 3

Illustrated in this example is an embodiment wherein a cleavable linker is used to operably bind the functionalized fluorescent nanocrystals to the solid support matrix. The cleavable linker comprises two reactive functionalities, wherein each reactive functionality comprises an amine-reactive group (capable of binding an amine). Thus, one reactive functionality can be operably bound to an amine group of the solid support matrix, and a second reactive functionality can be operably bound to an amine group of a functionalized fluorescent nanocrystal. In this example, the solid support matrix comprised amine-activated spherical glass beads, and the functionalized fluorescent nanocrystals comprised semiconductor nanocrystals functionaized with a layer of homocysteine. 100 mg of 30–50 $\mu$m amine-activated spherical glass beads (non-porous) were diluted in 100 $\mu$l HEPES buffer (50 mM, pH 7). To this was added 9.1 $\mu$l of 10 mM DSP (cleavable linker) in dimethylsulfoxide (DMSO), and the mixture was stirred for 10 minutes. To the solid support matrix was added amine-activated functionalized fluorescent nanocrystals (100 $\mu$l, 10 $\mu$M), and the mixture was then stirred for 30 minutes. Ethanolamine was added to the solution to bring the concentration to 30 mM and stirring was continued for another 30 minutes. The solid phase were then washed with HEPES buffer, re-dispersed in DMSO, and placed on a microscope slide. After excitation with an excitation light source (ultraviolet illumination), the solid phase fluoresced because of the presence of the functionalized fluorescent nanocrystals operably bound thereto.

Following the formation of the solid phase, and the removal of any unbound components by washing the solid phase, the functionalized fluorescent nanocrystals were then cleaved from the solid support matrix. Various conditions were tested for the cleavage step in which a thiol is used to cleave the cleavable linker. In one illustrative example, the solid phase was reacted with 50 mM DTT (dithiothreitol) for one hour at room temperature. In another illustrative example, the solid phase was reacted with 50 mM DTT for one hour at 37° C. In another illustrative example, the solid phase was reacted with 50 mM mercaptoethanol for one hour at room temperature. In another illustrative example, the solid phase was reacted with 50 mM mercaptoethanol for one hour at 37° C. After the cleavage reaction in which the solid phase becomes solid support matrix and cleaved functionalized fluorescent nanocrystals, a solution comprising HEPES buffer was flowed through the solid support matrix in removing the cleaved functionalized fluorescent nanocrystals. The solid support matrix was then dispersed in DMSO, and placed on microscope slides for observation under ultraviolet illumination. In each case, fluorescence was not observed for the solid support matrix, indicating that the functionalized fluorescent nanocrystals were successfully cleaved, and then removed from the matrix, in accordance with the method of the present invention.

EXAMPLE 4

Illustrated in this example is an embodiment wherein ion-pairing comprises the reactive functionalities operably binding functionalized fluorescent nanocrystals to solid support matrix in forming the solid phase. Additionally, illustrated is a preferred embodiment wherein functionalized fluorescent nanocrystals are further functionalized in the solid phase by the addition of affinity ligand thereto, and the resultant product of the reaction is then purified from free affinity ligand that may be present in the solid phase after the reaction. Also illustrated is a unique advantage of the preferred functionalized fluorescent nanocrystals which are functionalized by the addition of a plurality of molecules selected from the group consisting of an amino acid, a carboxylic acid, and a combination thereof. More particularly, preferred molecules comprising amino acid typically comprise two types of reactive functionalities (e.g., a free amino group, and. a free carboxyl group) which may be used to selectively operably bind the desired component of the system of the present invention (e.g., use of the amino groups to operably bind the functionalized fluorescent nanocrystals to the solid support matrix, and use of the carboxyl groups to operably bind the functionalized fluorescent nanocrystals to free affinity ligand; or alternatively, use of the carboxyl groups to operably bind the functionalized fluorescent nanocrystals to the solid support matrix, and use of the amino groups to operably bind the functionalized fluorescent nanocrystals to free affinity ligand). The solid support matrix comprised amine-activated, controlled-pore glass beads (average size of the beads selected from the group consisting of 74–125 $\mu$m, and 125–177 $\mu$m). The functionalized fluorescent nanocrystals comprised semiconductor nanocrystals functionalized with a layer of homocysteine. The ion-pairing comprised electrostatic interactions between the positively charged amino groups on the glass beads, and the negatively charged carboxylate groups on the functionalized fluorescent nanocrystals, wherein the ion-pairing is capable of being destabilized (e.g., disrupted) at a high pH (e.g., about pH 12.0; and more preferably, >12.3 pH). The affinity ligand used to further functionalize the functionalized fluorescent nanocrystals comprised neutravidin.

In this example, functionalized fluorescent nanocrystals (not having affinity ligand operably bound thereto; 416.7 $\mu$l of a 10 μM solution) were operably bound by ionic pairing to the solid support matrix by adding small portions of the glass beads to the solution of functionalized fluorescent nanocrystals in a reactor until the absorbance (at the peak emission spectrum of the fluorescent nanocrystal, which in this case was 536 nm) of the supernatant is near zero (e.g., 0.002 or less), indicating that substantially all of the functionalized fluorescent nanocrystals were operably bound to the solid support matrix in forming a solid phase which settled in the reactor. The resultant immobilized solid phase was washed well with a buffer solution, then redituled in the buffer solution (500 μl HEPES buffer). The solid phase was then contacted with various solutions in successive steps as follows. EDC (79.88 μg) and sulfo-NHS (22.6 μg) were contacted with the solid phase for 10 minutes. Mercaptoethanol, at a concentration of 20 mM, was contacted with the solid phase for 5 minutes. Neutravidin (at a 1:1 molar ratio with the functionalized fluorescent nanocrystals) was contacted with the solid phase for 2 hours. Ethanolamine, to a concentration of 30 mM, was contacted with the solid phase for 30 minutes. Typically, at this point 10% to 50% of the affinity ligand comprises free affinity ligand, representing an amount which may significantly impair the sensitivity of a diagnostic assay utilizing functionalized fluorescent nanocrystals.

The solid phase was then washed several times with a solution (e.g., HEPES buffer) to remove excess reagents and free affinity ligand. The wash step was performed until the absorbance (at 280 nm for detecting any free affinity ligand comprising neutravidin) of the flow through solution (flowed from the reactor containing the immobilized solid phase) reached near zero (e.g., 0.0X; where X is a number ranging from 0 to 9). The immobilized solid phase was then contacted with a solution of high pH (e.g., HEPES buffer, pH 12.38) which destabilized the ion-pairing, resulting in the detachment of functionalized fluorescent nanocrystals having affinity ligand operably bound thereto from the solid support matrix. The solution comprising the detached, functionalized fluorescent nanocrystals having affinity ligand operably bound thereto was collected from the reactor. The resultant preparation comprised functionalized fluorescent nanocrystals having affinity ligand operably bound which were substantially free of free affinity ligand. The resultant preparation may be concentrated, and neutralized to a pH of about 7, by placing the preparation in a centrifugal ultrafiltration tube (10 kD molecular weight cutoff) followed by ultrafiltration, and then addition of a solution of the desired pH (e.g., a buffer having a pH ranging from about 6.0 to about 8.0).

The functionalized fluorescent nanocrystals having affinity ligand operably bound which were substantially free of free affinity ligand, as produced and purified by the method according to the present invention, were tested for their sensitivity to identify the presence of a substrate, in modeling a diagnostic assay. More particularly, the neutravidin-functionalized fluorescent nanocrystals were tested for their sensitivity and ability to specifically bind a biotinylated substrate. A diagnostically effective amount of these functionalized fluorescent nanocrystals having affinity ligand operably bound thereto (5 μl of the neutralized solution described above) was mixed with a substrate comprising biotinylated polystyrene beads (5 μl; 1% solids). The volume of the mixture was brought up to 50 ml, and the mixture was then incubated for 30 minutes. The beads were harvested from the mixture by centrifugation, and then the beads were washed with HEPES, redispersed in DMSO, and placed on a microscope slide. After excitation with an excitation light source (ultraviolet illumination), the beads showed an even, and intense (brightness of) fluorescence because of the presence of the functionalized fluorescent nanocrystals operably bound thereto. The pattern and intensity of the fluorescence resulting from use of the functionalized fluorescent nanocrystals having affinity ligand operably bound thereto and purified according to the present invention indicated that they were quantifiably and significantly more sensitive than comparable (of the same nanocrystal type, the same affinity ligand, and the same conditions for coupling) functionalized fluorescent nanocrystals having affinity ligand operably bound thereto which were produced by conventional methods in the art (i.e., not purified according to the method of the present invention).

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed:

1. A process for purifying functionalized fluorescent nanocrystals having affinity ligand operably bound thereto by using a solid support matrix in a reactor through which solutions are circulated, wherein an immobilized solid phase is formed by operably binding functionalized fluorescent nanocrystals to the solid support matrix, wherein the solid phase is immobilized in the reactor, and wherein the solutions are flowed through the immobilized solid phase to purify the functionalized fluorescent nanocrystals having affinity ligand operably bound thereto.

2. The process according to claim 1, wherein the solid phase is formed outside the reactor, and then the solid phase is immobilized in the reactor.

3. The process according to claim 1, wherein the solid phase is formed inside the reactor.

4. The process according to claim 1, wherein the solutions flowed through the reactor, and which circulate through the immobilized solid phase, are flowed in a stepwise fashion.

5. The process according to claim 1, wherein the reactor is in the form of a column, and the solid support matrix comprises a particulate form.

6. The process according to claim 5, wherein the solid support matrix comprises beads which are packed in the column.

7. The process according to claim 1, wherein the functionalized fluorescent nanocrystals having affinity ligand operably bound thereto comprise semiconductor nanocrystals.

8. A solid phase, comprised of a solid support matrix operably bound to functionalized fluorescent nanocrystals having affinity ligand operably bound thereto, formed in the process according to claim 1.

9. A method for purifying functionalized fluorescent nanocrystals having affinity ligand operably bound thereto, the method comprising:

(a) contacting functionalized fluorescent nanocrystals with affinity ligand under suitable conditions for the functionalized fluorescent nanocrystals to become operably bound to affinity ligand in forming a mixture comprising functionalized fluorescent nanocrystals having affinity ligand operably bound thereto, and free affinity ligand;

(b) contacting the mixture with solid support matrix under suitable conditions for the solid support matrix to become operably bound to functionalized fluorescent nanocrystals having affinity ligand operably bound thereto in forming an immobilized solid phase;

(c) flowing a solution through the immobilized solid phase in a step of removing free affinity ligand from the solid phase;

(d) detaching the functionalized fluorescent nanocrystals, comprising functionalized fluorescent nanocrystals having affinity ligand operably bound thereto, from the solid support matrix; and (e) flowing a solution through the solid support matrix to remove from the solid support matrix the detached functionalized fluorescent nanocrystals having affinity ligand operably bound thereto in yielding purified functionalized fluorescent nanocrystals having affinity ligand operably bound thereto.

10. The method according to claim 9, wherein the solid phase is formed outside of a reactor, and then the solid phase is immobilized in the reactor in which the solutions are flowed through.

11. The method according to claim 9, wherein the solid phase is formed inside the reactor.

12. The method according to claim 9, wherein the solutions flowed through the reactor, and which circulate through the immobilized solid phase, are flowed in a stepwise fashion.

13. The method according to claim 10, wherein the reactor is in the form of a column, and the solid support matrix comprises a particulate form.

14. The method according to claim 13, wherein the solid support matrix comprises beads which are packed in the column.

15. The method according to claim 9, wherein the purified functionalized fluorescent nanocrystals having affinity ligand operably bound thereto comprise semiconductor nanocrystals.

16. A solid phase, comprised of a solid support matrix operably bound to functionalized fluorescent nanocrystals having affinity ligand operably bound thereto, formed in the method according to claim 9.

17. Purified functionalized fluorescent nanocrystals having affinity ligand operably bound thereto produced by the method according to claim 9, wherein the purified functionalized fluorescent nanocrystals having affinity ligand operably bound thereto are substantially free of free affinity ligand.

18. The method according to claim 9, wherein a solution is flowed through the solid phase, wherein the solution induces the detachment of functionalized fluorescent nanocrystals from the solid support matrix.

19. The method according to claim 18, wherein the solution used to induce detachment also comprises the solution used to remove detached functionalized fluorescent nanocrystals having affinity ligand operably bound thereto from the solid support matrix.

20. The method according to claim 9, wherein a cleavable linker is used to operably bind the solid support matrix to functionalized fluorescent nanocrystals having affinity ligand operably bound thereto in forming an immobilized solid phase; and wherein a cleaving agent for cleaving the cleavable linker is contacted with the solid phase under conditions suitable for cleavage of the cleavable linker in the step comprising detaching the functionalized fluorescent nanocrystals from the solid support matrix.

21. The method according to claim 9, wherein ion-pairing is used to operably bind the solid support matrix to functionalized fluorescent nanocrystals having affinity ligand operably bound thereto in forming an immobilized solid phase; wherein the ion-pairing comprises a bond which is disrupted by a high pH; and wherein a solution having a high pH is contacted with the solid phase under conditions suitable for disrupting the ionic bonding necessary for the functionalized fluorescent nanocrystals having affinity ligand operably bound thereto to remain operably bound to the solid support matrix in the step comprising detaching the functionalized fluorescent nanocrystals from the solid support matrix.

22. A method for purifying functionalized fluorescent nanocrystals having affinity ligand operably bound thereto, the method comprising:

(a) contacting functionalized fluorescent nanocrystals with solid support matrix under suitable conditions for the functionalized fluorescent nanocrystals to become operably bound to solid support matrix in forming an immobilized solid phase;

(b) contacting the solid phase with a solution comprising affinity ligand under suitable conditions for affinity ligand to become operably bound to functionalized fluorescent nanocrystals of the solid phase;

(c) flowing a solution through the solid phase in removing free affinity ligand from the solid phase;

(d) detaching the functionalized fluorescent nanocrystals, comprising functionalized fluorescent nanocrystals having affinity ligand operably bound thereto, from the solid support matrix; and (e) flowing a solution through the solid support matrix to remove from the solid support matrix the detached functionalized fluorescent nanocrystals having affinity ligand operably bound thereto in yielding purified functionalized fluorescent nanocrystals having affinity ligand operably bound thereto.

23. The method according to claim 22, wherein the solid phase is formed outside of a reactor, and then the solid phase is immobilized in the reactor in which the solutions are flowed through.

24. The method according to claim 22, wherein the solid phase is formed inside the reactor.

25. The method according to claim 22, wherein the solutions flowed through the reactor, and which circulate through the immobilized solid phase, are flowed in a stepwise fashion.

26. The method according to claim 22, wherein the reactor is in the form of a column, and the solid support matrix comprises a particulate form.

27. The method according to claim 22, wherein the solid support matrix comprises beads which are packed in the column.

28. The method according to claim 22, wherein the purified functionalized fluorescent nanocrystals having affinity ligand operably bound thereto comprise semiconductor nanocrystals.

29. A solid phase, comprised of a solid support matrix operably bound to functionalized fluorescent nanocrystals having affinity ligand operably bound thereto, formed in the method according to claim 22.

30. Purified functionalized fluorescent nanocrystals having affinity ligand operably bound thereto produced by the method according to claim 22, wherein the purified functionalized fluorescent nanocrystals having affinity ligand operably bound thereto are substantially free of free affinity ligand.

31. The method according to claim 22, wherein a solution is flowed through the solid phase, wherein the solution induces the detachment of functionalized fluorescent nanocrystals from the solid support matrix.

32. The method according to claim 31, wherein the solution used to induce detachment also comprises the solution used to remove detached functionalized fluorescent nanocrystals having affinity ligand operably bound thereto from the solid support matrix.

33. The method according to claim 22, wherein a cleavable linker is used to operably bind the solid support matrix to functionalized fluorescent nanocrystals having affinity ligand operably bound thereto in forming an immobilized solid phase; and wherein a cleaving agent for cleaving the cleavable linker is contacted with the solid phase under conditions suitable for cleavage of the cleavable linker in the step comprising detaching the functionalized fluorescent nanocrystals from the solid support matrix.

34. The method according to claim 22, wherein ion-pairing is used to operably bind the solid support matrix to functionalized fluorescent nanocrystals having affinity ligand operably bound thereto in forming an immobilized solid phase; wherein the ion-pairing comprises a bond which is disrupted by a high pH; and wherein a solution having a high pH is contacted with the solid phase under conditions suitable for disrupting the ionic bonding necessary for the functionalized fluorescent nanocrystals having affinity ligand operably bound thereto to remain operably bound to the solid support matrix in the step comprising detaching the functionalized fluorescent nanocrystals from the solid support matrix.

* * * * *